US006114603A

United States Patent [19]
Christou et al.

[11] Patent Number: 6,114,603
[45] Date of Patent: Sep. 5, 2000

[54] GENETIC ENGINEERING OF SUGARBEET PLANTS

[75] Inventors: Paul Christou, Norwich; Fatima Pelica, Bowthorpe, both of United Kingdom

[73] Assignee: John Innes Center, Norwich, United Kingdom

[21] Appl. No.: 09/049,142

[22] Filed: Mar. 27, 1998

[51] Int. Cl.$^7$ .............................. C12N 5/04; C12N 15/05; C12N 15/82; A01H 5/00

[52] U.S. Cl. ...................... 800/293; 435/430.1; 435/431; 435/470; 800/278; 800/300

[58] Field of Search .................................. 435/69.1, 410, 435/420, 430, 430.1, 431, 418, 419, 468, 470; 536/23.6, 24.1; 800/278, 288, 293, 295, 298, 300

[56] References Cited

U.S. PATENT DOCUMENTS

| 5,015,580 | 5/1991 | Christou et al. | 435/172.3 |
| 5,503,998 | 4/1996 | Christou et al. | 435/172.3 |
| 5,614,395 | 3/1997 | Ryals et al. | 435/172.3 |

FOREIGN PATENT DOCUMENTS

| 2301103 | 11/1996 | United Kingdom | C12N 9/18 |
| 91/00358 | 1/1991 | WIPO | C12N 15/87 |
| 92/17591 | 10/1992 | WIPO | C12N 15/56 |
| 93/07272 | 4/1993 | WIPO | C12N 15/29 |
| 96/29415 | 9/1996 | WIPO | C12N 15/56 |

OTHER PUBLICATIONS

Fromm et al, Biotechnology, vol. 8, pp. 833–839, 1990.
Abe, J., et al., "Tissue culture response of Beta germplasm: callus induction and plant regeneration," *Cell, Tissue, and Organ Culture*, vol. 27, pp. 123–127 (1991).
Atanassov, "Sugar Beet," in *Handbook of Plant Cell Culture*, (Evans, et al., eds. New York, 1986) pp. 652–680.
Bhat, et al., *J. Plant. Physiol.*, vol. 124, pp. 419–423 (1986).
Cai, D., et al., "Positional Cloning of a Gene for Nematode Resistance in Sugar Beet," *Science*, vol. 275, pp. 832–834 (1997).
Callis, et al., *Genes Dev.*, vol. 1, pp. 1183–1200 (1987).
Catlin, D.W., "The effect of antibiotics on the inhibition of callus induction and plant regeneration from cotyledons of sugerbeets (*Beta vulgaris* L.)," *Plant Cell Reports*, vol. 9, pp. 285–288 (1990).
Christou, P., "Genetic engineering of crop legumes and cereals: current status and recent advances,"*Agro–Food–Industry Hi–Tech*, pp. 17–27 (Mar./Apr. 1994).
Christou, P., "Stragegies for variety–independent genetic transformation of important cereals, legumes and woody species utilizing particle bombardment," *Euphytica*, vol. 85, pp. 13–27 (1995).
Christou, P., "Transformation Technology," *Trends in Plant Sciences*, vol. 1, pp. 423–431 (Dec. 1996).
Cocking, et al., "Gene transfer in Cereals," *Science*, vol. 236, pp. 1259–1262 (1989).

Cooley, et al., *Theor. Appl. Genet*, vol. 90, pp. 97–104 (1995).
Coumans–Gilles, et al., *Plant Cell Tissue Organ Culture*, pp. 93–101 (1981).
Creissen, G.P. et al., "Cloning and characterisation of glutathione reductase cDNAs and identification of two genes encoding the tobacco enzyme," *Planta* (1995).
De Block, M., et al., "Engineering herbicide resistance in plants by expression of detoxifying enzyme," *The EMBO Journal*, vol. 6, pp. 2513–2518 (1987).
De Block, M., et al., "Expression of foreign genes in regenerated plants and in their progeny," *The EMBO Journal*, vol. 3, pp. 1681–1689 (1984).
De Greef, et al., *Plant. Sci. Lett.*, vol. 17, pp. 55–61 (1979).
Detrez, et al., *J. Exp. Bot.*, vol. 39 (204), pp. 917–926 (1988).
Detrez, et al., *Theor. Appl. Genet.*, pp. 462–468 (1989).
D'Halluin, K., et al., "Transformation of Sugarbeet (*Beta Vulgaris* L.) And Evaluation of Herbicide Resistance in transgenic Plants," *Bio/Technology*, vol. 10,pp. 309–314 Mar. 1992).
Doctrinal, et al., *Plant Cell, Tissue and Organ Culture*, pp. 1–12 (1989).
Doley, et al., *Plant Cell Reports*, vol. 8, pp. 222–225 (1989).
Ehlers, U., et al., "Cloning of the coat protein gene from beet necrotic yellow vein virus and its expression in sugar beet hairy roots," *Theor. Appl. Genet.*, vol. 81, pp. 777–782 (1991).
Eide, et al., *North Dakota Acad. Sci. Proc.*, vol. 45, pp. 37 (1991).
Farago, et al., *Genetika A Slechteni*, vol. 25, pp. 215–222 (1989).
Freason, et al., *Dev. Biol.*, vol. 33, pp. 130–137 (1973).
Freytag, et al., *Plant Cell Reports*, vol. 8, pp. 647–650 (1990).
Freytag, A.H., et al., "An improved medium for adventitious shoot formation and callus induction in *Beta vulgaris* L. in vitro," *Plant Cell Reports*, vol. 7, pp. 30–34 (1998).
Galatowitsch, et al., *Can J. Plant. Sci.*, vol. 70, pp. 83–89 (1990).
Gamborg, et al.,*Exp. Cell Res.*, vol. 50, pp. 151–158 (1968).
Hooker, M.P., et al., "Callus Initiation, Growth, and Organogenesis in Sugarbeet (*Beta vulgaris* L.)," *Z. Pflanzenphysical. Bd.*, vol. 84, pp. 237–246 (1997).
Horsch, et al., "Inheritance of Functional Genes in Foreign Plants.".
Horsch, et al., "A Simple and General Method for Transferring Genes into Plants," *Science*, vol. 227 (Mar. 8, 1995).
Hussey, et al., *Ann. Bot.*, vol. 42, pp. 477–479 (1978).

(List continued on next page.)

*Primary Examiner*—David T. Fox
*Assistant Examiner*—Ashwin Mehta
*Attorney, Agent, or Firm*—Greenblum & Bernstein, P.L.C.

[57] ABSTRACT

Methods for the transformation of sugarbeet which include the use of cyclical regeneration of the target plant and particle bombardment. Such methods allow for genotype-independent transformation. These methods further allow for a stably transformed sugarbeet plant. Plants produced in accordance with these methods are provided as well.

31 Claims, 5 Drawing Sheets

OTHER PUBLICATIONS

Jacq, et al., *Plant Breeding*, pp. 185–191 (1993).
Jacq, et al., *Plant Cell Rep.*, vol. 11, pp. 329–333 (1992).
Jacq, B., et al., "Factors influencing T–DNA transfer in Agrobacterium—mediated transformation of sugarbeet," *Plant Cell Reports*, vol. 12, pp. 621–624 (1993).
Jefferson, R.A., et al., "GUS fusions: β–glucuronidase as a sensitive and versatile gene fusion marker in higher plants," *The EMBO Journal*, vol. 6, pp. 3901–3908 (1987).
Jones, et al., *Transgenic Research*, vol. 1, pp. 285–297 (1992).
Kallerhoff, J., et al., "Beet necrotic yellow vein virus coat protein–mediated protection in sugarbeet (*Beta vulgaris* L.) protoplasts," *Plant Cell Reports*, vol. 9, pp. 224–228 (1990).
Kao, et al., *Planta (Berl.)*, vol. 126, pp. 105–110 (1975).
Klein, T.M., et al., "High–velocity microprojectiles for delivering nucleic acids into living cells", *Nature*, vol. 327, pp. 70–73 (1987).
Krens, et al., *J. Exp. Bot.*, vol. 45, pp. 1899–1901 (1994).
Krens,F.A., et al., "The effect of exogenously–applied phytophormones on gene transfer efficiency in sugarbeet (*Beta vulgaris* L.)," *Plant Science* vol. 116, pp. 97–106 (1996).
Krens,F.A., et al., The role of Explant Source and Culture Conditions on Callus Induction and Shoot Regeneration in Sugarbeet (*Beta vulgaris* L.),*J. Plant. Physiol.*, vol. 134, pp. 651–655 (1989).
Krens, F.A., et al., "Transformation and regeneration in sugar beet (*Beta vulgaris* L.) induced by 'shooter' mutants of *Agrobacterium tumefaciens*," *Euphytica*, vol. S, pp. 185–194 (1988).
Lenzner, et al., *Physiologia Plantarum*, vol. 94, pp. 342–350 (1995).
Lindsey, et al., *J. Exp. Bot.*, vol. 41, pp. 529–536 (1990).
Lindsey, et al., *Plant Mol. Biol.*, vol. 10, pp. 43–52 (1987).
Lindsey, K., et al., "Stable transformation of sugarbeet protoplasts by electroporation," *Plant Cell Reports*, vol. 8, pp. 71–74 (1989).
Li–Su–Nam, *Biologia plantarum*, vol. 18, pp. 389–392 (1976).
Longo, et al., *Plant. Sci. Lett.*, vol. 16, pp. 51–57 (1979).
Mahn, A., et al., "transient gene expression in shoot apical meristems of sugarbeet seedlings after particle bombardment," *Journal of Experimental Botany*, vol. 46, pp. 1625–1628 (1995).
Matzk, et al., *Mol. Plant–Microbe Interact*, vol. 9, pp. 373–381 (1996).
McCabe D., et al., "Direct DNA transfer using electric discharge particle acceleration ( ACCELL™ technology)," *Plant, Tissue and Organ Culture*, vol. 33, pp. 227–236 (1993).
Miedema, *Euphytica*, vol. 31, pp. 635–643 (1982).
Mikami, *Euphytica*, vol. 40, pp. 271–273 (1989).
Moffat, A.S., "First Nematode–Resistance Gene Found," *Science*, vol. 275, pp. 757 (1997).
Murashige, T., et al., "A Revised Medium for Rapid Growth and Bio Assays with Tobacco Tissue Cultures," *Physiologia Plantarum*, vol. 15, pp. 473–497 (1962).
Negrutiu, et al., *Plant Science Letters*, vol. 5, pp. 293–304 (1975).
Owens, et al., *Plant Cell, Tissue and Organ Culture*, vol. 26, pp. 127–133 (1991).
Owens, et al., *Plant Cell, Tissue and Organ Culture*, vol. 31, pp. 195–201 (1992).
Potrykus, I., "Gene Transfer to Plants: Assessment of Published Approaches and Results," *Annu. Rev. Plant Physiol. Plant Mol. Bio.*, vol. 42, pp. 205–225 (1991).
Ramanathan, et al., *Plant Mol. Biol.*, vol. 28, pp. 1149–1154 (1995).
Ritchie, et al., *J. Exp. Bot.*, vol. 42, pp. 277–283 (1982).
Saunders, et al., *Crop Science*, vol. 22, pp. 1102–1105 (1982).
Saunders, et al., *Crop Science*, vol. 26, pp. 1240–1245 (1986).
Saunders, et al., *Crop Science*, vol. 32, pp. 1357–1360 (1992).
Saunders, J.W., et al., "One Step Shoot Regeneration from Callus of Whole Plant Leaf Explants of Sugarbeets Lines and a Somaclonal Variant for_in vitro Behavior," *J. Plant. Physiol*, vol. 124, pp. 473–479 (1986).
Stomp, A–M., "Histochemical Localization of β–Glucuronidase," *GUS Protocols: Using the GUS Gene as a Reporter of Gene Expression* , pp. 103–113 (1992).
Szabados, et al., *Plant Cell Rep.*, vol. 4, pp. 195–198 (1985).
Tenning, et al., *Plant Science*, vol. 81, pp. 103–109 (1992).
Tetu, et al., *J. Exp. Bot.*, vol. 38, pp. 506–517 (1987).
Thorens, et al., "Chloroquine and ammonium chloride prevent terminal glycosylation of immunoglobulins in plasma cells without affecting secretion," *Nature*, vol. 321 (1986).
Van Den Elzen, P., et al., "A chimaeric hygromycin resistance gene as a selectable marker in plant cells," *Plant Molecular Biology*, vol. 5, pp. 299–302 (1985).
Van Geyt, et al., *Plant Cell Reports*, pp. 66–69 (1985).
Van Geyt, et al., *Theor. Appl. Genet.*, pp. 920–925 (1987).
Welander, *Physiol. Plant.*, vol. 32, pp. 305–307 (1974).
Welander, *Physiol. Plant.*, vol. 36, pp. 7–10 (1976).
Wozniak, et al., *Physiologia Plantarum*, vol. 90, pp. 763–771 (1994).
Yannisch–Perron, et al., *Gene*, vol. 33, pp. 103–119.

pWRG2426

SLJ1006

GENETIC ENGINEERING OF SUGARBEET PLANTS

BACKGROUND OF THE INVENTION

1. Field of the Invention

The present invention relates to the genetic transformation of sugarbeet plants. Specifically, the present invention is directed to a genotype-independent transformation of sugarbeet plants. The present invention utilizes bombardment techniques in the transformation.

2. Background of the Invention and Related Information

Sugarbeet is economically the most important sucrose-producing crop in temperate regions of the world and provides about 37% of the world's sugar. In addition, the sugarbeet plant is useful in the production of many other commercially important carbohydrates.

In contrast to many other plant species, sugarbeet has proven recalcitrant to regeneration after transformation. Some plants are totipotent, in that entire plants can be regenerated from a single plant cell, and transgenic plants can, therefore, be engineered from genetically engineered plant cells. However, many reports have demonstrated that the regeneration of sugarbeet after transformation is difficult to reproduce, is unpredictable and is strongly genotype dependent.

A number of effective DNA-delivery systems are available for the transfer of foreign genes into plant genomes. Effective gene transfer into sugarbeet using the gram-negative soil bacterium Agrobacterium has been demonstrated. However, Agrobacterium-based transformation of sugarbeet is confined to relatively few genotypes. Regeneration from tissue culture following Agrobacterium infection has also proved difficult with somaclonal variation resulting from tissue-culture induced mutations. Several patent applications are directed to the subject of Agrobacterium-mediated transformation of sugarbeets, including U.S. Pat. No. 5,614,395 to RYALS et al., PCT International Application PCT/DK92/00108 to MIKKELSEN et al., and World Intellectual Property Organization Application No. WO 93/07272 to LETHAM. RYALS et al., MIKKELSEN et al., and LETHAM, are hereby expressly incorporated by reference as though set forth in full herein.

A number of studies have indicated that Agrobacterium-mediated transformation may result in two problems which need to be addressed prior to the release of any genetically engineered plant into the environment. First, molecular analysis of genomic DNA from plants engineered in this manner has suggested the presence of vector sequences outside the transferred DNA borders (RAMANATHAN et al., *Plant Mol. Biol.* 28, pp. 1149–1154 (1995)). In addition, the Agrobacterium microbe has been found to persist on the surface and within tissues of soil-grown transformed plants up to 12 months following transformation (MATZIK et al., *Mol. Plant-Microbe Interact.* 9, pp. 373–381 (1996)). These two problems make the use of Agrobacterium in sugarbeet transformation considerably less attractive.

Other methods of transforming plants include directly transferring DNA by using electroporation or chemical fusagens such as polyethylene glycol with calcium phosphate. World Intellectual Property Organization Application No. WO 91/00358 to JØRSBOE teaches a method for introducing genetic material into plant cells such as tobacco and sugarbeet using ultrasound treatment. Each of these methods, however, requires the use of protoplasts, and as noted above, regeneration of sugarbeet plants from single cells has proven to be very difficult. Even in cases in which regeneration from single cells has been reported, genotype specificities can severely hinder the transformation and regeneration of these crops. DNA can also be effectively transferred via the mechanical introduction of plasmid DNA via microinjection. Although this method is not subject to host-range limitations, regeneration from single cells is a requirement. In view of the foregoing, there is a need for a method to stably introduce DNA into sugarbeet plant cells without having to regenerate from single cells.

Particle bombardment is a technique that has proven effective in the genetic transformation of other species of plant. This technique utilizes very small particles which are delivered at a high velocity. The particles act as carriers of biologically active DNA into germline plant cells, tissues, and organs. Particle bombardment has been successfully employed for the transformation of soybean (U.S. Pat. Nos. 5,015,580 and 5,503,998 to CHRISTOU et al., the entire contents of which are expressly incorporated by reference as though set forth in full herein) and other crops refractory to alternative gene transfer methods. MAHN et al. demonstrated transient gene expression using particle bombardment of sugarbeet in *J. Experimental Botany* 46 (291), pp 1625–1628 (1995), the entire content of which is hereby incorporated by reference as though set forth in full herein. However, to date, particle bombardment has not successfully been used to create a stably transformed sugarbeet.

SUMMARY OF THE INVENTION

In accordance with the present invention, it has surprisingly been found that particle bombardment of a proliferative cyclically regenerating sugarbeet shoot culture system can result in the stable integration of transgenes into a host genome. Further, in accordance with the present invention, the transformation of the sugarbeet plants is genotype-independent. Still further, in accordance with the present invention, the sugarbeet plants are regenerated from growing sugarbeet shoots in culture.

In view of the foregoing, the present invention is directed to methods of making a genetically transformed sugarbeet plant comprising preparing a transgene; attaching the transgene to a substantially biologically inert carrier particle to form at least one coated particle; producing at least one cyclically regenerated sugarbeet shoot; and forcing the at least one coated particle into the at least one cyclically regenerated sugarbeet shoot. Preferably, the transgene comprises at least one expression construct, which preferably comprises at least one coding sequence and at least one regulatory sequence. The at least one regulatory sequence may comprise a promoter, which preferably comprises a member selected from the group consisting of cauliflower mosaic virus 35s promoter with intron from maize alcohol dehydrogenase gene, cauliflower mosaic virus 35s promoter, cauliflower mosaic virus 35s promoter with alfalfa mosaic virus leader, and nopaline synthase promoter from *Agrobacterium tumefaciens*. The at least one regulatory sequence may comprise a terminating signal, which preferably comprises a member selected from the group consisting of nopaline synthase polyadenylation signal from *Agrobacterium tumefaciens*, and soybean polyadenylation signal. The at least one coding sequence may comprise at least one marker gene, which preferably comprises a selectable gene which comprises a member selected from the group consisting of bialaphos resistance gene, aminoglycoside-3-phosphotransferase II gene, and aminoglycoside phosphotransferase IV gene. The selectable gene may comprise a bialaphos resistance gene, the presence of which is preferably verified by assay. In alternative preferred embodiments, the at least one marker gene comprises a detectable gene, which preferably comprises a member selected from the group consisting of luciferase gene, jellyfish green fluorescent protein gene, and β-D-glucuronidase gene. When the β-D-glucuronidase gene is used, its presence may be verified by assay. In still other preferred embodiments, the at least one marker gene comprises a selectable gene and a detectable gene. Methods are provided for genotype-independent sugarbeet transformation.

Preferably, the carrier particles used in accordance with the present methods comprise metal. This metal may include a member selected from the group consisting of gold, tungsten, iridium, ruthenium, rhodium, platinum, palladium, and alloys thereof. In accordance with the present methods, the at least one cyclically regenerated sugarbeet shoot is preferably derived from at least one embryonic axis of a sugarbeet seed. Preferably, the sugarbeet seed comprises a zygotic embryo. In preferred embodiments, regeneration is performed in RV medium. Preferably, regeneration is also performed in MS medium. In preferred embodiments of the present invention, the shoots comprise sugarbeet cells at differing stages of the cell cycle.

The present invention is also directed to progeny population of a transgenic sugarbeet plant species comprising a stably integrated transgene in the progeny genome, wherein the transgene was stably integrated into the parent genome in a process comprising a cyclic regeneration system and particle bombardment. The progeny may be propagated via self-pollination.

A sugarbeet cell in a cyclically regenerated sugarbeet plant comprising an inert metal particle coated with exogenous genetic material is also provided. In still other embodiments, a sugarbeet cell comprising a stably integrated exogenous expression construct, which sugarbeet cell contains no extraneous vector non T-DNA is provided.

A sugarbeet shoot comprising a stably integrated expression construct that will not release Agrobacterium onto the surface or within the tissues of soil-grown transformed plants following regeneration is provided in accordance with the present invention. The present invention also provides a sugarbeet plant comprising a stably expressing exogenous transgene regenerated in the absence of protoplasts or callus culture.

In accordance with the present invention, a sugarbeet germline cell comprising a stably integrated transgene is provided. Preferably, a sugarbeet plant is derived from the germline cell and expresses the transgene. A sugarbeet plant which comprises progeny of such a sugarbeet plant is provided.

Also provided is a sugarbeet plant comprising cyclically-regenerated plant tissue and a substantially biologically inert carrier particle and a transgene. In addition, a sugarbeet plant comprising (a) a substantially biologically inert carrier particle, and (b) a transgene, and (c) a germline cell comprising the transgene stably integrated into the genome of said germline cell is provided. Preferably, the sugarbeet plant comprises Beta vulgaris L. Var. Saccharifera (Altissima), a biennial plant of the genus Beta L., family Chenopodiaceae.

In accordance with the present invention, a stably transformed sugarbeet plant comprising a transgene, which transgene exists in the genome of said plant in the substantial absence of Agrobacterium genetic material is provided.

In still other embodiments of the present invention, sugarbeet leaf tissue comprising germinating seedlings which seedlings comprise at least one stably integrated transgene is provided. Also provided is a genetically transformed sugarbeet plant, comprising at least one stably integrated transgene, wherein the plant has expressed the transgene for a period of at least one week, or more preferably, at least two weeks. Even more preferably, the period is at least four weeks. The period may extend to at least eight weeks, or even at least sixteen weeks.

Also provided is a method of preparing a sugarbeet plant for genetic transformation comprising excising at least one embryo from at least one sugarbeet seed; culturing the at least one embryo; culturing a shoot apex which grows in culture from the at least one embryo; culturing a first plant tissue growth which grows in culture from the shoot apex; and culturing a second plant tissue growth which grows from the first plant tissue growth. Preferably, the embryo is cultured for at least about 8 days prior to culturing the shoot apex, or even more preferably, at least about 10 days prior to culturing the shoot apex. Preferably, the shoot apex is cultured for at least about 14 days prior to culturing the first plant tissue growth. Also preferred, the first plant tissue growth is cultured for about 14 days prior to culturing the second plant tissue growth.

These and other features of the present invention will become apparent from the following specification.

While not wishing to be bound by theory, it appears that by forcing the transgene into cyclically regenerating sugarbeet shoots that are simultaneously at different stages of the cell cycle, there is a greater likelihood that the DNA will be stably integrated into those sugarbeet cells that are at the receptive stage of the cell cycle. It is believed, for these reasons, that the present invention succeeds where the prior art fails in the stable transformation of the recalcitrant sugarbeet plant.

BRIEF DESCRIPTION OF THE DRAWINGS

The foregoing and other objects, features, and advantages of the invention will be apparent from the following more particular description of the invention, as specifically illustrated in the accompanying drawings wherein.

DETAILED DESCRIPTION OF THE INVENTION

Figure 1:
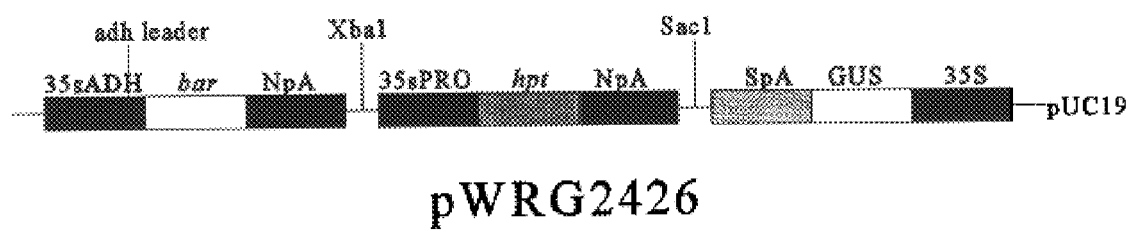
FIG. 1 is a schematic representation of plasmid pWRG2426.

The present invention is directed to methods of genetically transforming sugarbeet plants. In accordance with the present invention, DNA in the form of a transgene attached to a substantially biologically inert carrier particle to form a coated particle. The coated particle is physically delivered into individual cells of organized and regenerable sugarbeet tissue via particle bombardment. The particle bombardment is carried out in a manner that neither destroys nor incapacitates the target plant tissues. The transgene is incorporated into the genome of cells of the sugarbeet. The sugarbeets are then grown to adult plants, which express the transgene. Adult plants can produce progeny which also express the transgene.

In accordance with the present invention, several factors have been identified which appear to be important to the stable transformation of sugarbeets. The target sugarbeet tissue is preferably leaf tissue on which shoot primordia are present. Such tissue is prepared using a system of cyclical regeneration. The DNA is preferably carried into the cells by way of particles which are physically introduced into cells.

Many mechanisms exist for physically introducing particles into plant cells. Such mechanisms include centrifugal acceleration of particles, ballistic explosive acceleration of particles, electrostatic acceleration of particles, and any other manner of imparting velocity and momentum to particles. Any of these mechanisms may be used in accordance with the present invention. However, the most preferred mechanism is that set forth in detail herein, and is based on an adjustable electric voltage spark discharge device.

Particle Bombardment

For particle bombardment as used in accordance with the present invention, genetic material is first associated with a substantially biologically inert carrier particle. The carrier particle may comprise any substantially biologically inert material that may serve as a suitable attachment for the aforementioned genetic material. Preferably, the carrier particle comprises a material that is of relatively high density. Particles should be of high enough mass to possess adequate momentum to penetrate the plant tissue. Preferable materials for use in the particles include gold, tungsten, palladium, rhodium, platinum, iridium, and ruthenium, as well as other second and third row transition metals. Alloys of the foregoing metals are also acceptable. Most preferably, the carrier particle comprises gold. Materials chosen for use in the carrier particles should be chemically inert to prevent adverse reactions with the genetic material or the cellular material of the target tissue. Preferably, metals used in the carrier particles should be able to form organometallic complexes with DNA possessing the correct stereochemistry that will allow optimal dissociation of the metal-DNA entity once the particle enters the target cell.

The carrier particle is preferably roughly spherical in shape and microscopic in size. The particle diameter is preferably from about 0.1 micrometers (microns) to about 10 microns, and is more preferably from about 0.5 microns to about 5 microns. Most preferably, the particle is from about 1 micron to about 3 microns in diameter.

The genetic material may be attached to the carrier particle by any manner known in the art. Preferably, the genetic material is dried onto the carrier particles at a ratio of approximately 0.1–5 micrograms DNA per milligram of gold carrier particle. More preferably, the ratio is from about 0.25 to about 2.5 micrograms DNA per milligram gold carrier particle, and most preferably the ratio is from about 0.5 to about 1 micrograms DNA per milligram gold carrier particle.

In a preferred embodiment, the DNA may be attached to the carrier particles by precipitation. Preferably, 30 micrograms DNA and 30 milligrams of 1–3 micron diameter gold carrier particles are combined with 5 μl of 10 mM $Na_2HPO_4$. About 5 μl of 10 mM $CaCl_2$ is then added to form a $CaHPO_4$ precipitate as the solution dries. Preferably, the precipitate carries the DNA onto the carrier particles as it forms. In alternative preferred embodiments, EDTA may be added to the suspension. In still other preferred embodiments, spermidine may be added to the suspension. When the carrier particles and the phosphate and the calcium chloride have been mixed with the DNA, the suspension is preferably dried under a stream of $N_2$ with frequent stirring. Upon drying, the particles are ready to be used in the bombardment.

Particle bombardment may be accomplished using any particle bombardment protocol but is preferably performed according to the following procedures. The DNA-coated particles are prepared as described above and resuspended in ethanol. The suspension is sonicated briefly and injected into an appropriate length of teflon tubing (3 mm internal diameter). The particles are allowed to settle under gravity at room temperature for about 5 minutes. The ethanol is drained carefully by wicking with tissue paper. The tubing is then rotated at high speed (about 300 rpm) to distribute the particles about the inner circumference. It is important to dry the tubes as completely as possible before proceeding to the next step. Any residual moisture can result in uneven particle delivery during shooting, or in extreme cases will prevent dislodging of the particles by the He gas after firing. After drying the tube is cut in one-half inch segments ("charges") and stored dry at approximately –20° C. until used.

The loaded charges are inserted into a modified particle inflow gun (Corbett Scientific, Sydney, Australia) and the gun is connected to a Helium cylinder through high pressure metal tubing and charged to the appropriate pressure. It has been found that a pressure of approximately 450 psi is suitable. The accelerating force provided by rapid and instantaneous discharge of the trigger, which releases the appropriate He pressure. The gas pressure is subsequently directed through the charges holding the DNA-coated particles and it is this force that dislodges and accelerates the particles to impact the target tissue, at atmospheric pressure.

Another device for accelerating the particles is described in detail in U.S. Pat. No. 5,503,998, to CHRISTOU, the entire content of which is hereby expressly incorporated by reference as though set forth in full herein. A general description of the particle bombardment technique is set forth in MCCABE & CHRISTOU, *Plant Cell, Tissue and Organ Culture,* Vol. 33, pp. 227–236 (1993), the entire content of which is hereby expressly incorporated by reference as though set forth in full herein. Briefly, the apparatus consists of a spark discharge chamber into which are inserted two electrodes. Preferably, the electrodes are spaced approximately 0.5–2.5 millimeters apart. The spark discharge chamber comprises a horizontally extending rectangle having a first and second opening extending out its upward end. The first opening is covered by an access plate. The second opening is located on the side of the chamber opposite the electrodes, and is intended to be covered by a carrier sheet.

The electrodes are connected to a suitable adjustable source of electric discharge voltage. Preferably, such a source comprises electric switching connected to a capacitor of the one to two microfarad size range, with the amount of voltage introduced onto the capacitor being adjustable, such as through the use of an autotransformer, through the range of about 1 to about 50,000 volts. Preferably, high voltage switching is provided to allow the capacitor to be safely discharged through the electrodes, at the convenience of a user.

The carrier sheet to be placed over the second opening in the discharge chamber is preferably a planar sheet of relatively stiff material. Preferable materials include, but are not limited to, aluminized saran-coated mylar. Positioned approximately 15 millimeters above the second opening is a retaining screen. Positioned approximately 5 to 25 millimeters above the retaining screen is a target surface. The target surface may be any suitable surface onto which the material to be transformed may be placed, and is preferably a culture surface. More preferably, the target surface is a petri dish in which the target plant tissue has been positioned for culture.

Upon attachment of the genetic material to the carrier particles, the particles are resuspended in ethanol and placed onto the carrier sheet, which is inserted at the second opening to the spark discharge chamber. After settling of the beads, the ethanol is drained and the sheet dried. The target surface, including the target plant tissue (to be described in detail hereinafter), is placed in position over the retaining screen. A small droplet of water, preferably about 10 $\mu$l in size, is placed to bridge the ends of the electrodes. The access cover is placed in position over the first opening to the spark discharge chamber.

The entire apparatus is placed in a vacuum environment and a vacuum of from about 250 to about 500 millimeters Hg is created. More preferably, the vacuum is approximately 500 millimeters of Hg. Care should be taken to avoid vacuum pressures less than approximately 250 mm Hg, which can cause the target tissue to lose moisture with subsequent loss in cell viability. As the vacuum is created, a supply of He is bled into the vacuum environment. Preferably, the atmosphere surrounding the apparatus is saturated with He. While not wishing to be bound by theory, it appears that the lower relative density of the He in combination with the reduced pressure, helps to reduce drag on the particles.

After the environment surrounding the device is prepared as above, spark discharge between the electrodes may be initiated by a user. The force of the discharge bridges the spark discharge gap between the electrodes, vaporizing the water placed therebetween. The force of the vaporization of the water creates a shockwave which radiates outward. The shockwave impacts the carrier sheet, propelling the carrier sheet toward the retaining screen with great velocity. Upon impacting the retaining screen, the carrier sheet is stopped, while the carrier particles coated with genetic material continue toward the target. The carrier particles may penetrate cells of the target plant tissue upon contact.

The velocity of the carrier particles is dependent on the initial voltage applied to the electrodes. Therefore, by adjusting the voltage applied to the electrodes, and thereby, the force of vaporization of the water, the velocity of the carrier particles may be varied. Adjustments in this manner allow for variability in the depth of penetration of the carrier particles into the plant tissue. The bombardment is preferably preformed at a velocity such that the particles enter the cell but do not destroy it. Preferably, the particles pass both the cell wall and the cell membrane. Preferably the particle bombardment is performed at accelerating voltage of about 10 to about 24 Kv.

The apparatus is preferably tested and adjusted so that appropriate penetration can be achieved. A preparation of approximately 1% w/v agar provides a good estimation of the purely physical, non-biological, behavior of the carrier particles. For example, the apparatus may be completely assembled and prepared for normal use, but, instead of target tissue, a preparation of 1% w/v agar is used as the target. By measuring depth of penetration as a function of voltage, a user can make the appropriate adjustments to the apparatus.

Obviously, the apparatus may also be tested and adjusted by using plant tissue as the target, and measuring the transformation efficiency using carrier particles coated with a marker gene. Alternatively, the particle penetration in the target tissue can be measured. While the tuning of the apparatus using plant target tissue can be more time consuming than using 1% agar as the target, the results can be much more valuable and telling of the appropriate conditions. Most preferably, tuning is a two-step process. First, the apparatus is coarsely tuned by using 1% w/v agar as the target. Second, the apparatus is tuned with plant tissue as the target, using carrier particles which carry a marker gene. Expression of the marker gene is evaluated. Using any tuning technique alone, or any combination of the techniques, one can easily determine the appropriate operating conditions.

The number of particles physically placed into each target cell can be an important consideration. The lower limit is preferably that which is necessary to result in incorporation of the genetic material into the genome. The upper limit is that which will cause physical damage to the cell resulting in cell destruction. Any number of particles which fall between these limits may be appropriately used. Preferably, about one to two particles are placed into each target cell.

In the present invention, target cells are part of the target sugarbeet plant. The target cells may be a part of any portion or section of a target plant. Preferably, the target plant tissues comprise germplasm. Preferably, such target tissues comprise shoots which are preferably produced by cyclic regeneration from a primary explant. Most preferably, the target plant tissue is young leaf tissue comprising forming shoots.

Cyclic Regeneration

Cyclic regeneration comprises a method for preparing and maintaining a supply of plant tissue at a stage of development which is especially responsive to genetic transformation. However, because of the inexact nature of plant molecular biology, cyclic regeneration is difficult to precisely define. Specifically, it is difficult to identify the precise time at which plant tissue is receptive to such transformation. This section describes the methods by which sugarbeet plant tissue may be prepared such that it is receptive to genetic transformation. In an attempt to better explain the technology, the term cyclic regeneration is used to describe the process.

As used herein, the term "cyclic regeneration" is synonymous with "cyclical regeneration." These terms may be used interchangeably. Plants may be said to be "cyclically regenerating." Plants or plant tissue grown using a "cyclic regeneration" process are said to have been "cyclically regenerated."

Figure 5:
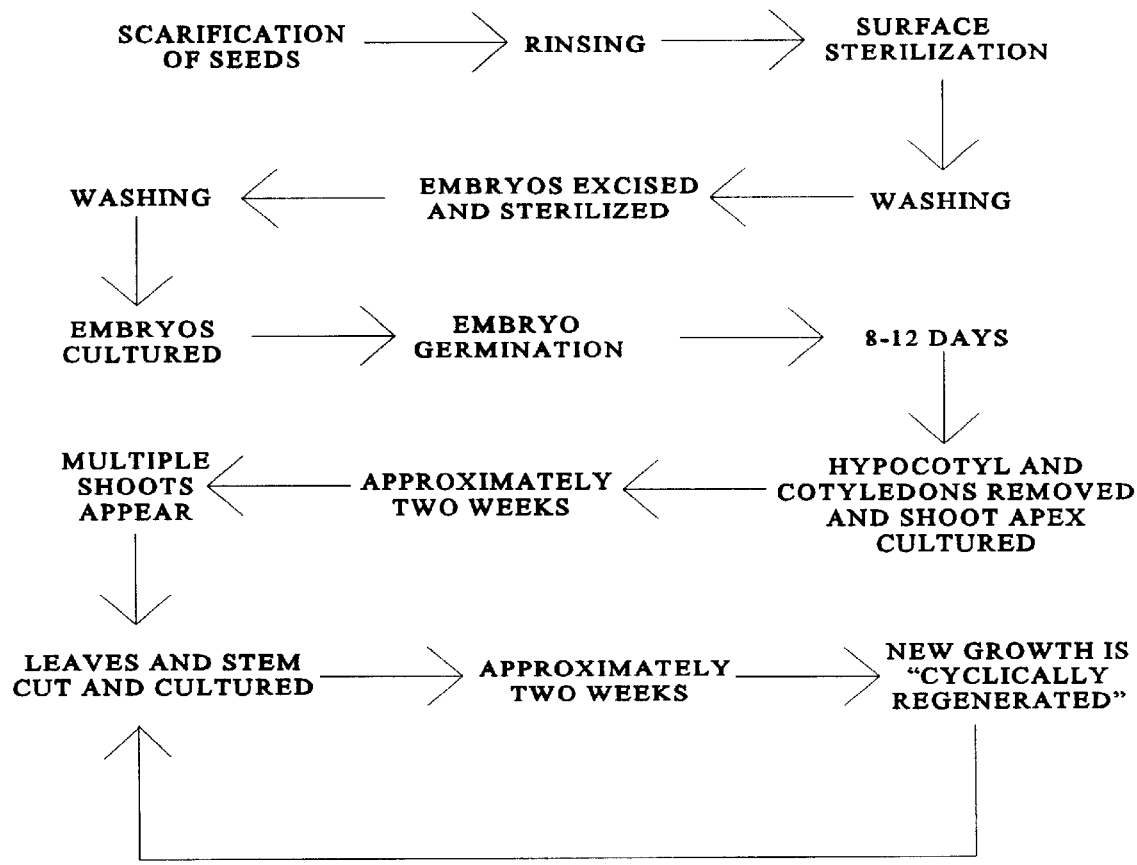
FIG. 5 is a schematic illustration of the cyclic regeneration process in accordance with the present invention.

The cyclic regeneration process of the present invention is illustrated schematically in FIG. 5. Note that FIG. 5 does not include all of the details of the cyclic regeneration process; to do so would unnecessarily clutter and confuse the diagram.

The procedure begins by scarification of seeds of the plant to be cyclically regenerated. In the present invention, the seeds comprise sugarbeet seeds. Preferably the seeds comprise seeds of an elite sugarbeet variety. Most preferably, the seeds comprise seeds from an experimental sugarbeet available from Van Der Have Research, Rilland, The Netherlands. Scarification of the seed is preferably performed by immersion in an acid. Preferably, the acid comprises concentrated sulfuric acid. The scarification process is performed for from about 25 minutes to about 75 minutes, and is preferably performed for about 50 minutes.

After scarification, the acid is rinsed from the seeds and the seeds are sterilized. Rinsing is preferably performed by rinsing the seeds under running water for a period of between about 15 to about 20 hours. More preferably, the seeds are rinsed for about 16–18 hours. The seeds are preferably surface sterilized in an ethanolic solution. Preferably the sterilization solution is 70% ethanol (w/v). Sterilization is preferably performed for a period of from about 1 to about 10 minutes, and 5 minutes is most preferred.

Following surface sterilization, the seeds are then washed repeatedly. Preferably, the washing comprises rinsing the seeds three times in sterile distilled water, followed by immersion in a hypochlorite solution with a detergent. Preferably, the hypochlorite solution with a detergent comprises 10% sodium hypochlorite plus 1 drop Tween 20 per 100 ml solution. Immersion in this solution is preferably performed for about 5 to about 15 minutes. Most preferably the immersion period is 10 minutes. The seeds are subsequently rinsed three times with sterile distilled water.

Mature embryos are excised from the seeds and sterilized by immersion in a sterilization solution. Preferably, the sterilization solution comprises hypochlorite and a detergent. Most preferably, the sterilization solution comprises 1% sodium hypochlorite and 1 drop Tween 20 per 100 ml sterilization solution. Sterilization is preferably performed by immersion in this solution for a period of from about 10 to about 20 minutes. Most preferably sterilization is performed for 15 minutes. The embryos are then washed three times in sterile distilled water, and then cultured in petri dishes containing an acceptable plant cell culture medium. Preferably, the plant cell culture medium comprises RV medium (FREYTAG et al., *Plant Cell Reports* 7, pp. 30–34 (1988)) supplemented with 7.0 g/l Phytagel (Sigma catalog #P8169) to overcome vitrification problems. All cultures are incubated at a fixed temperature in a light-dark cycle. Preferably, the culture temperature is about 23° C. to about 25° C., and is most preferably about 24° C. The light-dark cycle is preferably 17:7.

Between about 8 and about 12 days after embryo germination, preferably about 10 days after embryo germination, the hypocotyl and cotyledons are removed and the intact shoot apex cultured in fresh medium. Preferably the medium is RV medium. Multiple shoots appear approximately two weeks later. Although not preferable, this plant tissue may be used as target tissue for particle bombardment. More preferably, the plant tissue is re-cultured, as described in the next paragraph, prior to particle bombardment.

From the multiple shoots, leaves are removed and the main shoot is cut vertically in about two to three segments. The leaves and cut segments are then cultured, preferably in Magenta boxes containing RV medium. Preferably, the Magenta boxes are Magenta GA-7 vessels (Sigma catalog #V8505). Preferably, the new growth of plant tissue that appears after approximately two weeks is the first tissue which can be considered cyclically regenerated plant tissue. Any plant tissue which is grown therefrom is considered to have been cyclically regenerated. This procedure is preferably repeated at approximately two-week intervals. Leaves showing regeneration competency are removed and transferred to Magenta boxes containing RV medium. Multiple shoots growing on leaves are excised. The base of regenerable leaves is then cut in about two to three segments and re-cultured on fresh RV medium to continue the cyclic regeneration cycle. Plant tissue, and preferably leaf tissue, produced in this manner is a preferred target for particle bombardment in accordance with the present invention.

Bombarded plant tissues may be grown to adult plants. Bombarded plant tissue is preferably regenerated on RV medium until shoot growth appears, which is usually about two weeks after bombardment. The shoots are excised and grown on media containing the necessary components. Media which meet these requirements include, but are not limited to, MS medium supplemented with NAA. Preferably the plant growth medium is MS medium (Sigma catalog #M5519) (MURASHIGE & SKOOG, *Physiologia Plantarum*, Vol. 15, 1962, pp. 473–497) supplemented with 25 g/l sucrose, 7.0 g/l Phytagel (MS1) plus 1.5 mg/l naphthalene acetic acid (NAA).

Roots develop in about two weeks and plantlets may be potted and placed in a growth room at about 22° C. to about 25° C. on a 17:7 light-dark cycle. Plants are preferably covered with a plastic cup for maintenance of a high degree of humidity.

While not wishing to be bound by theory, it appears that the bombardment of cyclically regenerating (or cyclically regenerated) plant tissues increases the likelihood of stable integration of the foreign DNA into the host genome. This regeneration system can thus be successfully used in combination with bombardment technology to successfully transform sugarbeet plants. Using a system such as this maximizes the chances of bombarding at the correct stage of development to result in successful germline transformation of the sugarbeet plant.

Genetic Material

In accordance with the present invention, a transgene is delivered into the genome of cells of sugarbeet plants. The transgene preferably comprises an exogenous expression construct. The expression construct may comprise a chimeric construction, that is, with DNA originating from more than one organism. The expression construct may alternatively comprise a non-chimeric construct.

The expression construct comprises a coding sequence and a regulatory sequence. Such expression constructs may be embodied in expression cassette vectors for use in plant cells and are well known to those of ordinary skill in the art. The regulatory sequence preferably comprises a suitable promoter capable of promoting transcription and expression in vivo in plant cells, a transcription terminator capable of signaling the end of transcription, and a translation terminator suitable to terminate translation of messenger if protein synthesis is desired. Preferable promoters include, but are not limited to, the cauliflower mosaic virus 35s promoter with intron from maize alcohol dehydrogenase gene (35sADH), the cauliflower mosaic virus 35s promoter (35sPRO), the 35s promoter with alfalfa mosaic virus leader (35sAMV), and the nopaline synthase promoter from *Agrobacterium tumefaciens*. Preferable terminators include, but are not limited to, the nopaline synthase polyadenylation signal from *Agrobacterium tumefaciens* (NpA), and the soybean polyadenylation signal (SpA).

Preferably, the coding sequence comprises a marker gene. The marker gene is preferably selected based on its usefulness in the application. The marker gene may code for the expression of a substance that is detectable or selectable. In preferred embodiments, the marker gene codes for the expression of a selectable substance. Selectable substances include, but are not limited to, those substances that allow the plant expressing the substance to survive under a given set of conditions. Preferable selectable genes include, but are not limited to, those genes that code for antibiotic or herbicide resistance. Examples of such genes include the bialaphos resistance (bar) gene, the aminoglycoside-3-phosphotransferase II (APH 3'II) gene, and the APH IV gene. Expression of the bar gene allows for growth in the presence of phosphinothricin (PPT) or glufosinate ammonium; expression of the aminoglycoside phosphotransferase IV (APH IV) gene allows for growth in the presence of hygromycin; and expression of the APH 3'II gene allows for growth in the presence of aminoglycoside antibiotics such as kanamycin. The most preferred selectable gene is bar.

In alternative preferred embodiments, the marker gene codes for the expression of a detectable substance. Detectable marker genes may code for the expression of a phenotypic trait which is observable. Detectable substances include, but are not limited to fluorescent, phosphorescent, or other visibly apparent compounds. Examples of such substances include GFP (green fluorescent protein from jellyfish). The detectable substance also may comprise, but is not limited to, enzymes which catalyze the formation of fluorescent, phosphorescent, or other visibly apparent compounds. Preferred enzymes include, but are not limited to, firefly luciferase. Other enzymes that are useful in this regard include β-D-glucuronidase (GUS). The GUS gene (gusA) encodes a stable enzyme that is not normally present in plants and that catalyzes the cleavage of a range of β-D-glucuronides. The GUS activity in transformed plant tissues can be localized by observing the blue color that is formed after the hydrolysis of the uncolored substrate 5-bromo-4-chloro-3-indoyl β-D-glucuronic acid.

A combination of two or more marker genes may be used in accordance with the present invention. For example, a genetic construct may contain two selectable genes (e.g., resistance to two different herbicides/antibiotics) and a single detectable gene (e.g., production of a visibly apparent product). These genes could be used to screen sequentially, i.e., in the presence of one herbicide/antibiotic, then the other herbicide/antibiotic, then assay for the presence of the detectable gene product. Alternatively, the genes could be used to screen simultaneously, i.e., the two herbicides/antibiotics are both present in the growth medium, and the conditions are appropriate for detection of the detectable gene product, all at the same time. Any combination of selectable and detectable genes may be used in accordance with the present invention. In addition, any combination of assay (e.g., simultaneous or sequential) may be used in accordance with the present invention.

A combination of selectable and detectable genes is also envisioned. Such markers may be combined in a single plant cell by co-transfection, in which two separate constructs are used, each construct comprising either a selectable or a detectable gene. Alternatively, a chimeric construct may be prepared, in which both a selectable and detectable gene are present in a single plasmid vector. Marker genes and other genes of interest may be combined in similar manners, that is, by co-transformation using different vectors, or by preparing a single vector which comprises all the necessary genes.

As noted above, the expression construct may be chimeric or non-chimeric. Non-chimeric genes are especially useful when they already contain the necessary regulatory sequences.

In addition to the marker genes, the expression construct may further comprise other genes which code for the expression of any substance of interest.

Assays for Determining Transformation Efficiency

Although the present procedure is designed to maximize the number of plant cells which receive the foreign DNA, and to maximize the stable integration of the DNA into the genome of the plant cells, it should be recognized that not all of the targeted plant cells will have taken up the DNA into their genome. For this reason, it is often desirable to assay the plants, at various stages of development, for the presence or absence of a marker gene. For example, as noted above, the expression construct which is to be inserted into the plant genome preferably comprises a gene of interest and a marker gene. The marker gene may code for, for example, β-D-glucuronidase (GUS), a stable enzyme that is not normally present in plants and that catalyzes the cleavage of a range of β-D-glucuronides. The GUS activity in transformed plant tissues can be localized by observing the blue color that is formed after the hydrolysis of the uncolored substrate 5-bromo-4-chloro-3-indoyl β-D-glucuronic acid. Because this assay is destructive, however, it is necessary to balance the need for determining the presence of the marker gene with the necessary loss of plants required for such determination.

Alternatively, biochemical assays for the presence of the inserted genetic material or the expression product may be performed. For example, a suitable screening method for the existence of the DNA itself is the "Southern" blot hybridization technique. The presence of an expression product can often be demonstrated using a "Western" blot technique, when antibodies to the product of interest are available. Many such assays exist and are well known to those of ordinary skill in the art.

The foregoing procedures allow for the stable transformation of sugarbeet plants. Such stably transformed plants may reproduce and pass transgenic material to progeny plants.

Another unique aspect of the present invention is that, unlike plants transformed with, for example, Agrobacterium, plants transformed according to the present invention will not have Agrobacterium colonies growing on their surface or in their tissues. The growth of Agrobacterium on or in plants transformed with Agrobacterium can be a major drawback of methods in which Agrobacterium are used in transformation.

In addition, infection based methods of transformation can leave the plant with extraneous vector non T-DNA, which is also transferred to the plant in the infection/transformation process. This extraneous vector non T-DNA can be an unwanted remnant of the transformation process. The present invention, on the other hand, leaves the plant with only that DNA which is a part of the construct.

The present invention is advantageous in that genetically transformed plants can be produced from multicellular plant tissue. There is no need to grow plants from a single cell. Plants transformed in accordance with the present invention are produced without having to rely on growth from protoplasts or callus culture.

The foregoing specific embodiments are illustrative of applications in which methods of genetically modifying sugarbeet plants in accordance with the present invention can be employed. Those of ordinary skill in the art will readily understand that other manners of transformation are suitable and are in accordance with the present invention as well.

Without further elaboration, it is believed that one skilled in the art can, using the preceding description, utilize the present invention to its fullest extent. The following preferred working examples are, therefore, to be construed as merely illustrative, and not limitative of the remainder of the disclosure in any way whatsoever.

WORKING EXAMPLES

Example 1

Description of Vectors and Plasmid Maps

A first plasmid, pWRG2426, is prepared according to the methods of Cooley et al. (*Theor. Appl. Genet.* 90, pp. 97–104 (1995)), the entire contents of which is hereby incorporated by reference as though set forth in full herein. FIG. 1 shows a schematic representation of pWRG2426. This plasmid has the pUC19 backbone (YANISCH-PERRON et al., *Gene* 33, pp. 103–119) and contains the selectable bar gene encoding the enzyme phosphinothricin acetyltransferase (PAT) (DEBLOCK et al., *Embo J.* 6 (9), pp. 2513–2518, (1990)). The bar gene is flanked by the 35sADH promoter and the NpA termination sequence. The ADH intron and leader are enhancer elements which optimize expression. The pWRG2426 plasmid also contains the selectable hpt gene encoding hygromycin phosphotransferase (VAN DEN ELZEN et al. *Plant Mol. Biol.,* 5 pp. 299–302 (1985)), flanked by the 35sPRO promoter and the NpA terminator, and the gusA reporter gene encoding β-glucuronidase (JEFFERSON et al., *Embo J.* 6 pp. 3901–3908 (1987)) flanked by the 35sAMV promoter and the SpA terminator. All three genes of the first plasmid are under the control of the CaMV 35S promoter. Plasmid pWRG2426 contains hpt as the selectable gene flanked by two non-selected genes, bar and gusA. All three genes are driven by CaMV 35S promoter. The bar and hpt genes are transcribed in one direction and the gusA gene in the opposite direction. The bar gene has the maize Adh1 5'intron (Callis et al., *Genes Dev.* 1, pp. 1183–1200 (1987)) between the promoter and coding sequence. Bar and hpt have the nosA terminator and gusA has the ssu terminator.

Figure 2:
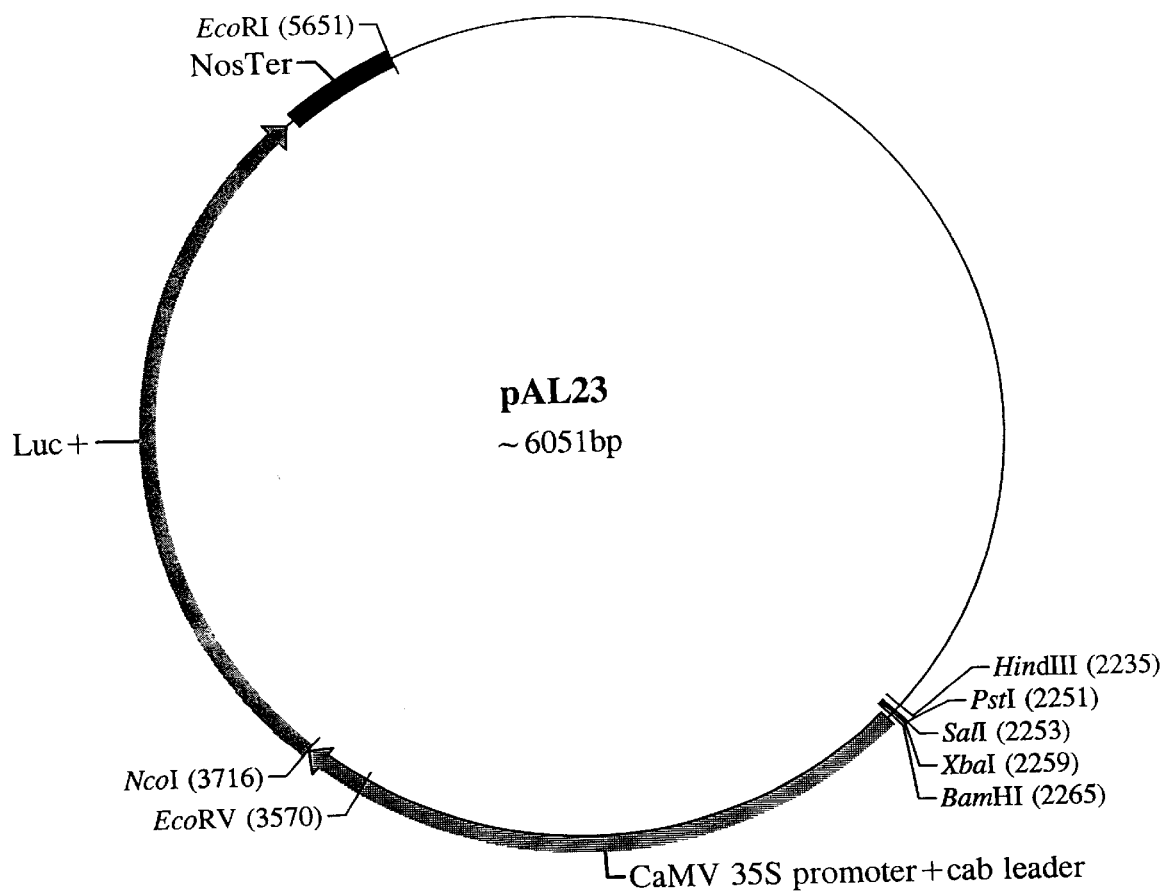
FIG. 2 is a schematic representation of plasmid pAL23.
Figure 3:
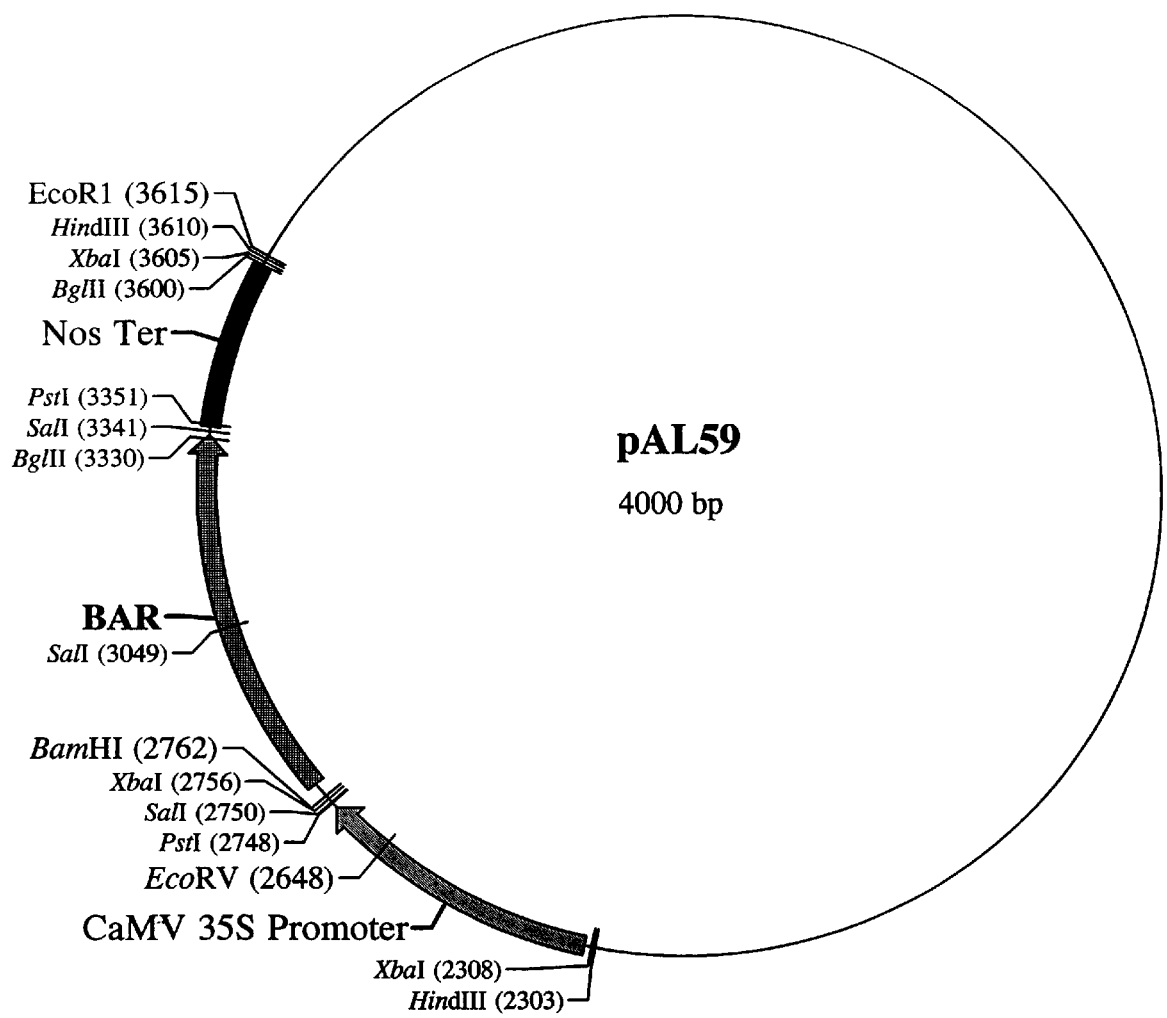
FIG. 3 is a schematic representation of plasmid pAL59.

A second plasmid, pAL23 (kindly provided by Alison Harvey, Cambridge Lab, JIC), contains the firefly luciferase (LUC+ in the Figure) gene driven by the CaMV 35S promoter. FIG. 2 shows a schematic representation of pAL23. The LUC gene also includes the nos terminator (Nos Ter in the Figure). A third plasmid, pAL59 (also provided by Alison Harvey, Cambridge Lab, JIC), contains the bialaphos resistance, bar, gene (BAR in the Figure) driven by the CaMV 35S promoter, and is flanked by the nos terminator. (The bar gene allows for the plant to grow in the presence of the antibiotic bialaphos.) FIG. 3 shows a schematic representation of pAL59.

Figure 4:
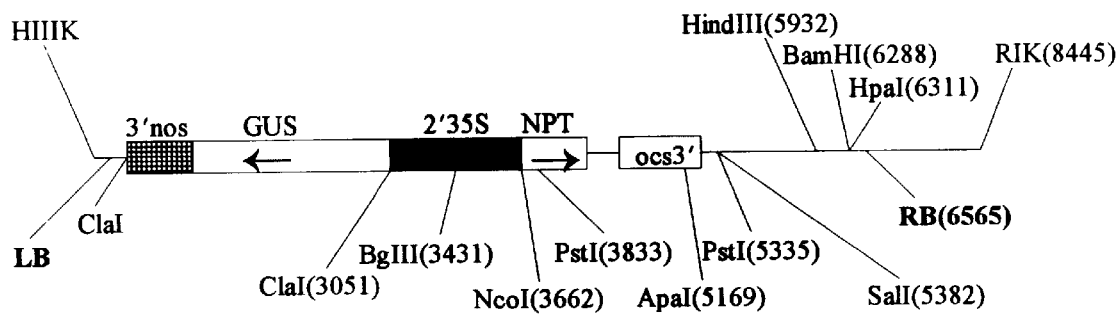
FIG. 4 is a schematic representation of plasmid SLJ1006.

A fourth plasmid, SLJ1006 (provided by Jonathan Jones, Sainsbury Lab, JIC), carries divergently gusA and NPT (neomycin phosphotransferase) genes driven by 2' and 35S promoters. (The NPT gene allows the plant to grow in the presence of the antibiotic neomycin.) FIG. 4 shows a schematic representation of SLJ1006. Plasmid SLJ1006 is prepared as described in Jones et al. (*Transgenic Research* 1, pp. 285–297 (1992)), the entire contents of which is hereby incorporated by reference as though set forth in full herein.

Example 2

Cyclic Regeneration System

Seeds of an elite sugarbeet variety (Van Der Have Research, Rilland, The Netherlands) are scarified by immersion in concentrated sulfuric acid for 50 minutes and washed for 16–18 hours under running water. The seeds are then surface sterilized using ethanol (70% w/v) for 5 minutes, rinsed 3 times in sterile distilled water, and immersed in 10% sodium hypochlorite plus Tween 20 (1 drop/100 ml solution), for 10 minutes. Subsequently, the seeds are washed 3 times with sterile distilled water.

Mature embryos are excised and sterilized by immersing in 1% sodium hypochlorite plus Tween 20 (1 drop/100 ml solution) for 15 minutes. Embryos are then washed 3 times in sterile distilled water and cultured in petri dishes containing RV medium (FREYTAG et al., *Plant Cell Reports* 7, pp 30–34 (1988)) with 7.0 g/l Phytagel (Sigma, catalog #P8169) to overcome vitrification problems. RV medium contains MS salts, 0.2 mg/l p-aminobenzoic acid, 0.4 mg/l ascorbic acid, 0.00025 mg/l D-biotin, 0.2 mg/l choline chloride, 0.015 mg/l folic acid, 0.5 mg/l niacin, 0.4 mg/l D-pantothenic acid, 0.5 mg/l pyridoxine HCl, 0.015 mg/l riboflavin, 0.5 mg/l thiamine HCl, 40.0 mg/l L-arginine (free base), 40.0 mg/l L-asparagine (anhydrous), 20.0 mg/l L-glycine, 60.0 mg/l L-glutamine, 20.0 mg/l L-phenylalanine, 40.0 mg/l L-tryptophan, 0.1 mg/l indole-3-butyric acid, 0.4 mg/l $N^6$-benzyladenine, and 25 g/l sucrose. The RV medium is adjusted to pH 5.8, solidified with agar (0.65%), and sterilized by autoclaving at 1.05 Kg/cm² for 15 min. All cultures are incubated at 24° C. under fluorescent light on an 17:7 light-dark cycle.

Ten days after embryo germination, the hypocotyl and cotyledons are removed and the intact shoot apex cultured in fresh RV medium. Multiple shoots appear 15 days later. Leaves are removed from the cyclically regenerated shoots, and the main shoot is cut vertically in 2 to 3 segments and cultured in Magenta boxes containing RV medium. Magenta boxes are Magenta GA-7 vessels (Sigma, catalog #V8505). This procedure is repeated at two-week intervals. Leaves are also cultured in petri dishes containing RV medium and transferred to fresh medium every 2 weeks. Leaves showing regeneration competency are transferred to Magenta boxes containing RV medium. Multiple shoots growing on leaves are excised. The base of regenerable leaves is then cut in 2 to 3 segments and re-cultured on fresh RV medium, to continue the cyclic regeneration cycle. Cyclically regenerated plant tissue produced in this manner is used as target tissue for bombardment.

Example 3

Transformation

Plasmids are multiplied in *E. coli* strain DH5 and isolated using the Qiagen Plasmid Maxi Kit (Qiagen Ltd, Surrey, U.K.). A total of 20 µg of DNA are coated onto 5 mg of 0.95 micron gold particles (Alpha Chemicals Inc.) according to the method described in MCCABE & CHRISTOU (1993). Briefly, this procedure entails loading the DNA onto the gold particles in the presence of $CaCl_2$ and spermidine to precipitate the DNA onto the gold. The coated beads are gently centrifuged and resuspended in 100% ethanol, then pipetted onto carrier sheets (18 mm×18 mm squares of ½ mil metalized mylar; DuPont 50MMC). After a brief period for settling, the ethanol is drained and the sheet dried.

The ACCELL apparatus is prepared by placing a 10 µl drop of water between the electrodes. The spark chamber is then covered with the access plate. The carrier sheet is laid over the top of the second opening and the retaining screen put in place.

Explants (shoot apex, petiole, multiple-shoot bases) are excised and pre-cultured on MS1 medium for 2, 4, 6, 16, and 24 hours, or MS1 medium supplemented with 0.5M mannitol, 2, 4, and 8 hours before bombardment. The target tissue is placed on an inverted petri dish, above the carrier sheet and the carrier particles. The assembly is then evacuated to 600 millibars and the discharge activated.

Bombarded explants are transferred to MS1 media with 3 mg/l PPT or RV medium with 3 mg/l PPT 1, 2, 3, and 5 days after bombardment. Necrotic tissue is removed every 3 weeks over a two to three month period. Green tissue is subcultured on fresh selection medium. Material that survives PPT selection is transferred to RV medium for regeneration.

Selection using an alternative selectable marker (hygromycin) is also performed. Explants are transferred to MS1 media plus 10 mg/l hygromycin or RV media plus 10 mg/l hygromycin 1, 2, 3, and 5 days after bombardment. Necrotic tissue is removed every 3 weeks over the following two to three month period. Green tissue is subcultured on fresh selection medium. Material that survives hygromycin selection is transferred to RV medium for regeneration.

Finally, the antibiotic kanamycin is also used for selection. Bombarded explants are transferred to MS1 medium plus 150 mg/l kanamycin or RV medium plus 150 mg/l kanamycin 1, 2, 3, and 5 days after bombardment. Necrotic tissue is removed every 3 weeks over the following two to three month period. Green tissue is subcultured on fresh selection medium. Material that survives kanamycin selection is transferred to RV medium for regeneration.

Following regeneration, plantlets are excised from multiple shoots and cultured individually on MS medium (MURASHIGE & SKOOG, *Physiologia Plantarum*, Vol. 15, 1962, pp. 473–497) supplemented with 25 g/l sucrose, 7.0 g/l Phytagel (MS1) plus 1.5 mg/l NAA. Roots develop in 2 weeks and the plantlets are potted and placed in a growth room at 22–25° C. on a 17:7 light-dark cycle. Plants are covered with a plastic cup for the first ten days to maintain a high degree of humidity.

Example 4

Demonstration of Stable Expression

The transgenic nature of regenerated plantlets is confirmed by expression of marker genes (selectable and detectable) and also by positive signals in the appropriate PCR reactions. Southern and Northern blot analyses confirm the long-term stability and expression of exogenous DNA.

β-Glucuronidase (GUS) Assay

GUS activity is assayed histochemically 24 to 48 hours after bombardment by scoring blue spots 8 to 24 hours after incubation in "GUS mix" (prepared as indicated in STOMP, in *GUS Protocols: Using the GUS Gene as a Reporter of Gene Expression*, pp. 103–113 (Academic Press, 1992)) at 37° C. GUS mix is 0.1M phosphate buffer, pH 7.0; 10 mM EDTA, pH 7.0; 1.0 mM X-Glucuronide; and 0.1% triton X-100. The complete procedure for assaying for GUS is presented in detail in JEFFERSON et al. (*Embo J.* 6, pp. 3901–3907 (1987)). Dithiothreitol (DTT) is added to the staining mix at a final concentration of 2 mM in order to eliminate phenoloxidase activity, which can interfere with the reaction (KRENS et al. *Plant Science*, 116 pp. 97–106 (1996)).

Luciferase (LUC) Assay

Explants are soaked in 1 mM luciferin (Promega, E160) solution made in ½ MS salts (200 mg/l $NH_4NO_3$, 32.5 mg/l KCl, 40 mg/l $KNO_3$, 6.25 mg/l $KH_2PO_4$, 72 mg/l $Ca(NO_3)_2.4H_2O$, 36 mg/l $MgSO_4.7H_2O$, 12.5 mg/l NaFe-EDTA, 0.8 mg/l $H_3BO_3$, 3.25 mg/l $MnSO_4.4H_2O$, 1.35 mg/l $ZnSO_4.7H_2O$, 0.375 mg/l KI) and supplemented with 0.01% triton X-100. Luciferase activity is assayed using a high performance luminescence imaging system Luminograph LB980 (EG&G Berthold, U.K.). Photon emission is measured during 57 seconds using cultures at 1 day, and 1, 2, and 4 weeks after bombardment.

PCR Analysis

DNA is isolated according to the method described in Creissen & Mullineaux (1995). PCR amplification of a 506 bp fragment of the bar gene is accomplished using the primer sequences: 5'-GGTCTGCACCATCGTCAACC-3' and 5'-CCCTGCAGTTACTATCAGATCTC-3'. PCR reactions are carried out in a PTC-200 DNA Engine™ Thermal Cycler (MJ Research Inc.) using 0.3 µg DNA, 5 µM of each primer, 20 mM dNTPs, 150 mM $MgCl_2$, 1× Amplitaq DNA polymerase buffer and 2.5 units of Amplitaq DNA polymerase (Perlin-Elmer/Cetus) in a total reaction volume of 50 µl. Amplification is performed using the following conditions: 95° C. for 40 s, 60° C. for 30 s, and 72° C. for 40 s (36 cycles). Twenty µl of each reaction are analyzed in a 1× TBE 1.8% agarose gel. PCR products are stained with ethidium bromide.

From the foregoing descriptions, one skilled in the art can easily ascertain the essential characteristics of this invention, and without departing from the spirit and scope thereof, can make various changes and modifications to the invention to adapt it to various usages and conditions. Although the invention has been described with reference to particular embodiments, it is to be appreciated that various adaptations and modifications may be made and the invention is only to be limited by the appended claims.

We claim:

1. A method of making a genetically transformed sugarbeet plant comprising:
   preparing a transgene;
   attaching the transgene to a substantially biologically inert carrier particle to form at least one coated particle;
   producing at least one cyclically regenerated sugarbeet shoot via excising at least one embryo from at least one sugarbeet seed, culturing the at least one embryo, culturing a shoot apex which grows in culture from the at least one embryo, culturing a first plant tissue growth which grows in culture from the shoot apex, and culturing a second plant tissue growth which grows from the first plant tissue growth to obtain a cyclically regenerated sugarbeet shoot;
   forcing the at least one coated particle into the at least one cyclically regenerated sugarbeet shoot to obtain a transformed sugarbeet shoot; and regenerating a sugarbeet plant from said transformed shoot.

2. The method of claim 1, wherein the transgene comprises at least one expression construct.

3. The method of claim 2, wherein the expression construct comprises at least one coding sequence and at least one regulatory sequence.

4. The method of claim 3, wherein the at least one regulatory sequence comprises at least one promoter.

5. The method of claim 4, wherein the at least one promoter comprises a member selected from the group consisting of cauliflower mosaic virus 35s promoter with intron from maize alcohol dehydrogenase gene, cauliflower mosaic virus 35s promoter, cauliflower mosaic virus 35s promoter with alfalfa mosaic virus leader, and nopaline synthase promoter from *Agrobacterium tumefaciens*.

6. The method of claim 3, wherein the at least one regulatory sequence comprises a terminating signal.

7. The method of claim 6, wherein the terminating signal comprises a member selected from the group consisting of nopaline synthase polyadenylation signal from *Agrobacterium tumefaciens*, and soybean polyadenylation signal.

8. The method of claim 3, wherein the at least one coding sequence comprises at least one marker gene.

9. The method of claim 8, wherein the at least one marker gene comprises a selectable gene.

10. The method of claim 9, wherein the selectable gene comprises a member selected from the group consisting of bialaphos resistance gene, aminoglycoside-3-phosphotransferase II gene, and aminoglycoside phosphotransferase IV gene.

11. The method of claim 10, wherein the selectable gene comprises a bialaphos resistance gene.

12. The method of claim 11, wherein presence of the bialaphos resistance gene is verified by assay.

13. The method of claim 8, wherein the at least one marker gene comprises a detectable gene.

14. The method of claim 13, wherein the detectable gene comprises a member selected from the group consisting of luciferase gene, jellyfish green fluorescent protein gene, and β-D-glucuronidase gene.

15. The method of claim 14, wherein the detectable gene comprises β-D-glucuronidase gene.

16. The method of claim 15, wherein presence of the β-D-glucuronidase gene is verified by assay.

17. The method of claim 8, wherein the at least one marker gene comprises at least one selectable gene and at least one detectable gene.

18. The method of claim 8, wherein the at least one marker gene comprises at least two selectable genes.

19. The method of claim 8, wherein the at least one marker gene comprises at least two detectable genes.

20. The method of claim 1, wherein the method comprises genotype-independent transformation.

21. The method of claim 1, wherein the carrier particles comprise metal.

22. The method of claim 21, wherein the metal comprises a member selected from the group consisting of gold, tungsten, iridium, ruthenium, rhodium, platinum, and palladium, and mixtures thereof.

23. The method of claim 1, comprising regenerating in RV medium.

24. The method of claim 23, comprising regenerating in MS medium.

25. The method of claim 1, wherein the shoots comprise sugarbeet cells at differing stages of the cell cycle.

26. A progeny population of a transgenic sugarbeet plant species comprising a stably integrated transgene in the progeny genome, wherein the transgene was stably integrated into the parent genome in the process comprising a cyclic regeneration system and particle bombardment of claim 1.

27. A sugarbeet plant as claimed in claim 26, wherein the progeny was propagated via self-pollination.

28. A sugarbeet cell in a cyclically regenerated sugarbeet plant comprising an inert metal particle coated with exogenous genetic material, said plant produced by the process of claim 1.

29. A sugarbeet plant comprising cyclically-regenerated plant tissue and a substantially biologically inert carrier particle and a transgene, said plant produced by the process of claim 1.

30. A sugarbeet plant comprising (a) a substantially biologically inert carrier particle, and (b) a transgene, and (c) a germline cell comprising the transgene stably integrated into the genome of said germline cell, said plant produced by the process of claim 1.

31. The sugarbeet plant of claim 30 wherein the sugarbeet plant comprises *Beta vulgaris* L. Var. Saccharifera (Altissima), a biennial plant of the genus Beta L., family Chenopodiaceae.

* * * * *